United States Patent [19]

Chiquiar-Arias

[11] 4,391,273

[45] Jul. 5, 1983

[54] NON-REUSABLE, DISPOSABLE SYRINGES

[75] Inventor: Marcelo Chiquiar-Arias, Mexico City, Mexico

[73] Assignee: Mercantile & Technical Promotions Inc., New York, N.Y.

[21] Appl. No.: 288,264

[22] Filed: Jul. 30, 1981

[30] Foreign Application Priority Data

Aug. 8, 1980 [MX] Mexico ................................. 183508

[51] Int. Cl.$^3$ ............................................. A61M 5/00
[52] U.S. Cl. ................................................ 604/110
[58] Field of Search ............ 128/218 R, 218 S, 218 P, 128/218 PA, 218 N, 234, 215, 220, 221, 216

[56] References Cited

U.S. PATENT DOCUMENTS

| | | | |
|---|---|---|---|
| 3,134,380 | 5/1964 | Armao | 128/215 |
| 3,677,245 | 7/1972 | Welch | 128/218 S |
| 3,951,146 | 4/1976 | Chiquiar-Arias | 128/218 R |
| 3,998,224 | 12/1976 | Chiquiar-Arias | 128/218 R |
| 4,213,456 | 7/1980 | Bottger | 128/218 P |

Primary Examiner—John D. Yasko
Attorney, Agent, or Firm—Ladas & Parry

[57] ABSTRACT

The present invention refers to improvements in disposable items, particularly self-destructing or otherwise automatically non-reusable hypodermic syringes having a self-destructing element which is actuated during the injection stroke of the piston. The invention provides an upper stop member, generally provided by a plate with a circular hole having a diameter permitting withdrawal of the plunger but not the piston and also a cylindrical protuberance adjacent the injection end of the cylinder and extending beyond the cylindrical wall so as to shield the fingers of the user from a self-destructing pin forced through the bottom wall of the cylinder under completion of the injection stroke. A cover plate for said cylindrical protuberance having an interior hole for the injection needle is also shown.

9 Claims, 6 Drawing Figures

NON-REUSABLE, DISPOSABLE SYRINGES

REFERENCES TO OTHER PATENTS

This invention relates to improvements in self-destructible or otherwise non-reusable disposable syringes disclosed in Mexican Pat. No. 134,368 and corresponding U.S. Pat. Nos. 3,951,146 and 3,998,224.

BACKGROUND OF THE INVENTION

The present invention deals with the health hazard problem caused by the common disposable syringes when they are reused for self-administration by the users. The invention is particularly useful in preventing drug addicts from finding and using said disposable syringes for drug addiction purposes. These problems of current and worldwide interest were only partially solved by the self-nonreusable syringes of the above-mentioned patents since the user could intentionally and readily detach the self-destructing element from the syringe before using it, thereby permitting reuse. Some of these devices employed a puncturing pin attached to the syringe piston, which pin would puncture the bottom of the syringe to make it non-reusable after the completion of the injecting stroke of the piston. However, the resulting protruding pin could prick the fingers of the user, if he or she were not careful. Also in some instances the protruding pin could be extracted and the hole caused by it plugged so as to permit reuse of the syringe.

It is an object of the present invention to make the above devices more effective in insuring non-reusability of the disposable syringes, preferably, totally avoiding their possible reuse, even if the user would intentionally try to make the self-destructing element inoperable. It is a separate object to prevent the self-destructing element from accidentally causing harm to the user and also to make it more difficult to repair any break in the cylinder caused by a puncturing pin or the like.

DESCRIPTION OF THE INVENTION

The present invention deals with the problem regarding removing a self-destructing element from the piston of the syringe by providing oppositely disposed stop means adjacent the open end of the cylinder so as to make it impossible to withdraw the piston, containing the self-destructing elements, from the cylinder, whether said self-destructing element be a knife at the side of the plunger to slit a weakened side wall of the syringe or a puncturing means such as a pin at the bottom of the piston, as described above. The above stop means is most conveniently a rigid disc, such as made of rigid plastic or metal, adhered to the support flanges adjacent the open end of the cylinder and having an interior circular opening with a diameter at least as large as the circular disc of the plunger of the syringe but having a smaller diameter than the diameter of the piston, which is compressible, adjacent the forward side of the disc of the plunger. In the case of a circular opening, which is the preferred embodiment, the diametrically opposed contiguous portions of the interior perimeter of the opening itself constitute the oppositely disposed stop means. However, it is also possible to have, instead of a smooth interior perimeter, a sequence of two or more substantially equally spaced, radially inwardly extending projections, the inward portions of which define an inner circle at least as great in diameter as the diameter of the disc adjacent the plunger but less than the outer diameter of the piston. In this way the plunger itself can pass through the outer stopping element but the rubber or other compressible piston can only be removed with substantial difficulty, thereby causing it to be separated from the piston and remain inside of the cylinder when the user attempts to withdraw it from the cylinder.

As regards the puncturing pin attached to the bottom of the cylinder of the syringe, an annular protuberance is provided which extends sufficiently forwardly of the bottom wall of the cylinder as to protect the fingers of the user from the puncturing pin after it is actuated to puncture the bottom wall and thus make the syringe non-reusable. This protuberance is usually cylindrical in shape and can either be an extension of the cylindrical wall of the cylinder or be coaxially disposed therewith but have a small diameter. It is also convenient to provide a circular cover plate for the end of the annular protuberance so as to hide the puncturing pin from view and to make it even more difficult to attempt to close the hole formed thereby after retracting the plunger. Of course, the cylindrical extension in itself makes it difficult to perform these acts.

According to an embodiment of the invention, both the upper stopping element and the lower protuberance can be provided.

The protuberance adjacent the injection needle of the syringe is also particularly useful in enabling the use of a puncturing pin of sufficient length to puncture prior to reaching the end of the fuel stroke of the piston without concern regarding possible additional likelihood of harm to the user on final use of the syringe.

DETAILED DESCRIPTION OF THE INVENTION

Figure 1:
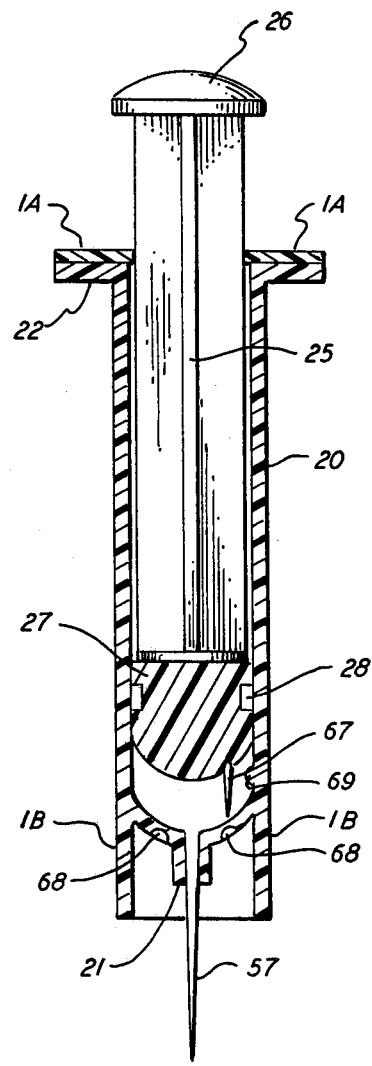
FIG. 1 is a side view of the syringe according to one embodiment of the invention in which the cylinder of the syringe as well as its cylindrical protuberance is in longitudinal cross-section as well as the piston, whereas the plunger is exposed. The puncturing pin is shown prior to puncturing the bottom of the cylinder.

With reference to the accompanying drawings, the improved syringes of the present invention include some of the elements described in the above U.S. and Mexican patents by the same inventor, which are repeated here with the same reference numerals while also including the new elements of the improvements which are numbered 1A, 1B, 2A and 2C.

Figure 2:
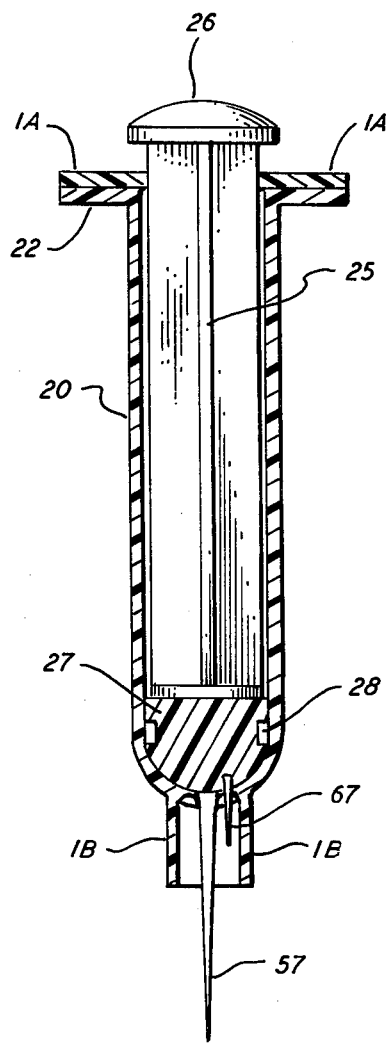
FIG. 2 is a similar view according to FIG. 1 of another embodiment with the cylindrical protuberance of a smaller diameter than the walls of the cylinder. Also the figure shows the final puncturing of the bottom wall of the cylinder.

The improved syringe of this invention, a specific embodiment of which is shown in FIGS. 1 and 2, comprises a cylinder 20 of a material capable of being perforated by a puncturing pin, such as plastic, and includes at its upper end a couple of ears 22, which project perpendicularly to the longitudinal central axis of the cylinder and are opposed so as to serve as support flanges for the user. The plunger of the syringe has a pair of flaps 25 intersecting in crosswise relationship and terminating at their upper end on a pressing disc 26, and, at their lower end, a piston 27 with annular sealing bosses 28.

This embodiment is applicable both to container-syringes (pre-filled syringes) and to empty syringes and includes at the front portion of the piston 27, a puncturing means, pin 67, oriented towards the front of the cylinder 20, parallel to the longitudinal axis of the syringe and coinciding with a groove 68 formed in the forward surface of the bottom wall in a circular shape so that the protruding pin 67 will always coincide with at least one portion of said circular groove. Said groove 68 weakens the bottom wall and facilitates, on completion of the stroke of the piston 27, when the solution is injected into the user, the puncturing of cylinder by the puncturing pin 67. In the case of empty syringes, a forward stop 69 is included, by which the person assembling this syringe can determine how far that person can extend piston 27 without having the pin 67 puncture the cylinder through the opening 68. It is obvious that when filling the syringe with the injectable solution, one will form an initial air gap, which can be eliminated before injection.

Figure 3:
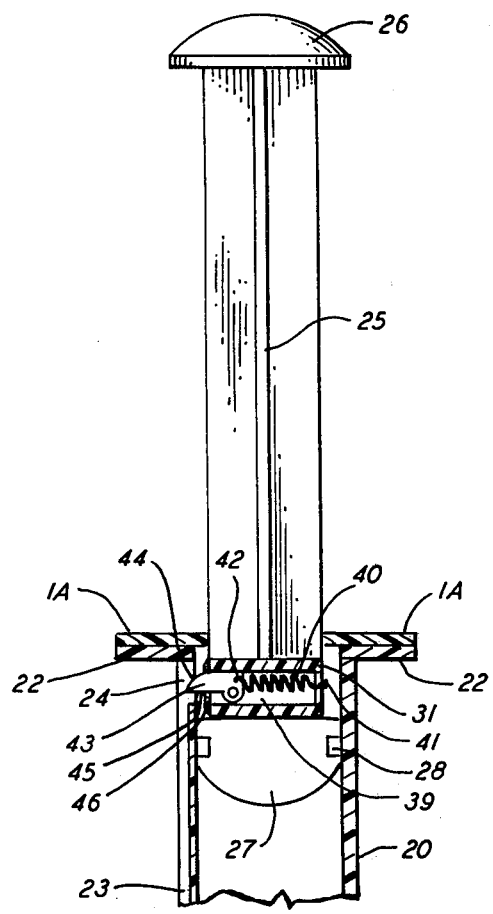
FIG. 3 is a similar partial cross-sectional view showing another embodiment of the invention having a knife at the side of the piston so as to cut a weakened longitudinal groove in the wall of the cylinder and illustrating stop means adjacent the open end of the cylinder to prevent removal of the piston from the cylinder.

The embodiment illustrated in FIG. 3 includes a slot or longitudinal weakening 23, in the exterior of cylinder 20, along practically the entire length of same, which has on its end adjacent the ears 22 a punctured portion 24, which penetrates the entire depth of the wall of the cylinder 20. The plunger composed of the flaps 25 includes a disc. Adjacent the disc in one of said flaps is formed a, preferably tubular, recess or seat 39, transverse to the longitudinal axis of the plunger. Compressible means, such as a helical spring 40, is lodged in said recess with one end 41 hooked to the base wall of the seat 39 with its other end 42 hooked to a knife 43, which has a rounded rear portion 44 and a straight front portion with a sharp edge 45. This knife goes through a cover plate 46, which closes the front end of the seat 39 and has a slot through which the knife 42 extends. Said slot has a length slightly greater than the height of the knife 43, which allows for a slight play of said knife, so when the plunger formed by flaps 25 is extracted in order to fill the syringe with solution, the knife is slightly displaced towards piston 27, contacting the wall of the cylinder with the rounded portion 44, whereby there will be no cutting of the wall of the cylinder. On the other hand, on the injection stroke, knife 43 will be displaced along the slot of the cover 46 to a position furthest from the base wall of the seat 39, thus forcing the sharp edge 49 in contact with the wall of the cylinder, cutting the cylinder 23 through the slot or weakening 23, to destroy the cylinder and avoid a subsequent reutilization of same. In this embodiment, it can be clearly observed that the knife does not need to reach the end of its run and project through the punctured portion 24, at the end of the weakened portion 23, in order to cut the cylinder since due to the play of the knife, the latter can cut the cylinder in any intermediate portion of the piston, even when the piston does not reach the maximum backward run. That is, with this embodiment the knife will cut in any position as long as the plunger is moved in a forward position towards the bottom wall of the cylinder, that is when injecting the solution with which the syringe was previously filled. Naturally if the knife 43 reaches perforation 24, allowing the knife to pass through said perforation, the cutting of the cylinder will be facilitated. Aside from the fact that the knife 43 is compressively mounted in the interior of the tubular housing 39, next to the disc 31, the rear support for piston 27, all the other structural elements of the syringe are similar to those of the embodiments described in FIGS. 1 and 2. To prevent rotation of the plunger about its axis protuberances are provided in the inner wall of the cylinder to contact a flap (21) other than that containing recess (39) similar to protuberances (29) of U.S. Pat. No. 3,951,146.

Another embodiment of the present invention combines the destructing effect of the puncturing pin with that of the cutting knife. It is also possible to have one or more self-destructing elements, whether a puncturing pin, a knife or any other type of self-destructing device as long as the cylinder is of a material, such as plastic, capable of being perforated or cut by said destructing elements during the normal injection stroke of the plunger or piston of the syringe. The hypodermic needle 57 can be joined by means of an appropriate adhesive to the bottom of the cylinder 20 or to a small projection 21 of same so that the injecting needle be integrally attached to the cylinder.

The safety element 1A which prevents the user from making the destructing element (blade 43) inoperative, such as by removal, comprises an external stopper 1A integrally joined to ears 22 of the cylinder, which stopper is affixed to said ears after assembling the syringe. The inner diameter of element 1A is less than the diameter of piston 27 and thus removal of the plunger together with the piston will cause the piston to be detached from the plunger and remain within the cylinder. The safety element 1B used to prevent the user from accidentally getting hurt with the puncturing pin 67 consists of a protecting annular, substantially rigid extension integral with the cylinder 20, which extension extends beyond the bottom of the cylinder, where said puncturing pin perforates the bottom wall of the cylinder on the completion of the injection. This protrusion also makes it difficult if not impossible for the hole formed by the protruding pin 67 to be plugged since there is little room for maneuvering within said protrusion 1B. Hypodermic needle 57, communicating with an opening at the bottom wall of cylinder 20 for the exit of the solution to be injected, extends beyond protrusion 1B a sufficient distance to permit the desired insertion of said needle into the patient. Also, a circular cover plate 2C, as shown in FIG. 4B, in connection with the embodiment of FIG. 4, can be used. The cover plate 2C, which can readily be a plastic or metal disc fused to the bottom of the circular protuberance, can make it substantially impossible to seal the hole caused by the puncturing pin 67.

Figure 4:
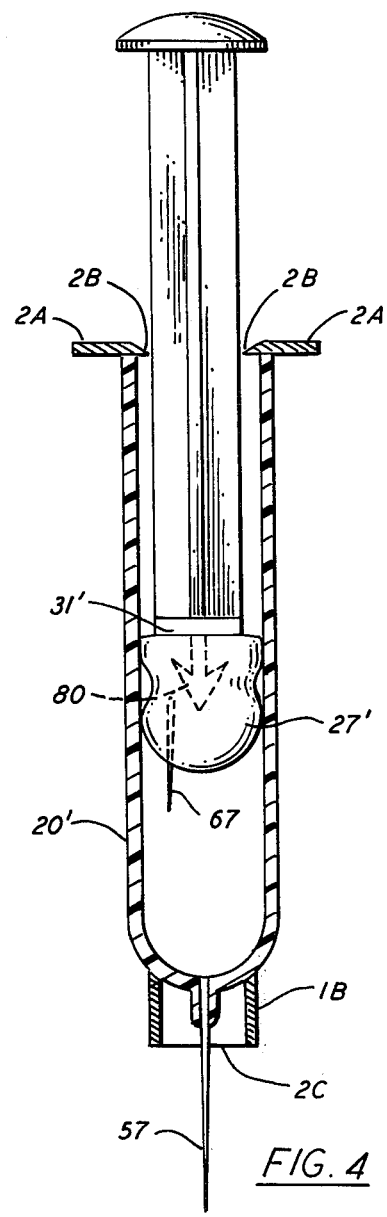
FIG. 4 illustrates another embodiment of the invention having a protruding pin extending forwardly of the compressible piston whereby removal of the piston is prevented by a combined stop means and support flanges.

FIG. 4 shows another embodiment of the invention in which piston 27' is of a substantially compressible material but has a rear edge of a substantially flat shape which makes it substantially impossible to withdraw the piston from the cylinder and thus attempt to remove the puncturing pin 67. Stop element 2A is a modified version of stop element 1A in that it is integrally formed with the ears 22' and furthermore has a frusto-conical opening with the diameter of the smallest opening, as defined by edge 2B with a diameter less than that of piston 27'. The sloping walls of the frusto-conical opening make it easy to insert the compressible rubber-like piston 27' into the cylinder but make it substantially impossible to remove the piston 27' from the cylinder. The rubber stopper is conveniently attached to the disc 31' of the plunger by a barb 80 embedded in the disc and extending into the rubber stopper.

As described above with relation to the embodiment of FIGS. 1 and 2, a cover 2C having a circular opening larger than the diameter of the injection needle 57 can be placed over the end of the cylindrical protuberance 1B, thereby making it substantially impossible to repair the hole formed in the bottom wall of cylinder 20'.

Although the invention has been described with respect to specific embodiments thereof, it should be understood by those skilled in the art that various changes or modifications in form or detail can be made without departing from the scope of the invention.

Figure 4A:
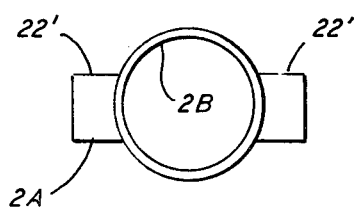
FIG. 4A gives a plan view of the combination support flanges and stop member and FIG. 4B shows a plan view of a cover element to be used in the cylindrical protuberance at the bottom portion of the cylinder.
Figure 4B:
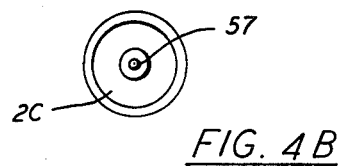

For example, stop element 2A can also replace the combination of ears 22 and stop element 1A in the embodiments of FIGS. 1, 2 and 3. Also the stop element as shown in plan view in FIG. 4A, could have a smaller interior diameter, larger than the exterior diameter of a smaller disc 31', wherein the outer edges of the flaps 35 could slideably fit in complementary matches in the interior opening 2B so as to prevent rotation of the plunger, rather than using the previously described protuberances 29.

I claim:

1. A disposable syringe which renders itself non-reusable which comprises a rigid cylinder having a bottom wall at one end with an opening for the exit of the solution to be injected, and having the other end open, support flanges being affixed to said cylinder adjacent the open end and extending outwardly from the axis of the cylinder, an injection needle integrally attached to the bottom wall of the cylinder and extending outwardly beyond said bottom wall and communicating with said opening, and a plunger with a piston slidably positioned within the cylinder with the piston adjacent the closed end of the cylinder and the other end of said plunger being adapted for pressing to force the piston toward the bottom wall, the piston having puncturing means extending longitudinally therefrom and adapted to puncture the bottom wall of said cylinder so as to prevent reuse, and an annular protrusion extending beyond the bottom wall of the cylinder and integral therewith and having such dimensions as to prevent the user's fingers from being pricked by the puncturing means extending through the bottom wall of the cylinder, said needle extending a sufficient distance beyond said annular protrusion to permit insertion of said needle in said patient, and which includes a cover plate for the opening at the forward end of the annular protrusion, said cover plate having a centrally disposed opening, said injection needle having a diameter less than the inner diameter of said opening in said cover plate and passing through said opening.

2. A syringe according to claim 1, in which the plunger has a circular disc adjacent the piston and has flaps extending outwardly from the axis of said plunger above and adjacent said disc, said cylinder having a longitudinal groove partially penetrating the wall of said cylinder, one of said flaps of said plunger being oppositely aligned with the weakened groove of the cylinder, there being a recess in said flap immediately adjacent said disc and adjacent said piston, said recess providing a transversely extending housing, there being compressible means positioned within said housing, a knife being attached to the radially outward end of said compressible means, said knife being positioned so as to cut the weakened portion of said wall when the plunger is pressed to force the piston toward the bottom wall of the cylinder, and oppositely disposed stop means affixed to the other end of the cylinder adapted to prevent movement of the piston out of the cylinder in the direction away from the bottom wall, said piston being of compressible material and having a diameter greater than the diameter of a circle defined by radially inward portions of the oppositely disposed means, and the disc adjacent the plunger having a diameter no greater than the diameter of the circle defined by radially inward portions of said oppositely disposed stop means, said stop means comprising a disc affixed to the support flanges having a circular opening with a diameter less than the diameter of the compressible piston but greater than the diameter of the disc adjacent the piston.

3. A syringe according to claim 2, in which the circular opening of the oppositely disposed stop means has a greater diameter at its upper end than at its bottom end, adjacent the open end of the cylinder, so as to have a frusto-conical shape with the diameter of the smallest opening being less than the diameter of the piston.

4. A syringe according to claim 3, in which the support flanges and oppositely disposed stop means are integrally formed.

5. A disposable syringe which renders itself non-resuable, which comprises a rigid cylinder having a bottom wall at one end with an opening for the exit of the solution to be injected, and having the other end open, said open end being integrally coupled to support flanges which extend outwardly from the cylinder walls, and a plunger comprising cross-wise arranged flaps with a disc at one end, said cylinder having a longitudinal groove partially penetrating the wall of said cylinder, one of the flaps of said plunger being oppositely aligned with the weakened groove of the cylinder, there being a recess in said flap immediately adjacent said disc of said piston, said recess providing a transversely extending housing, there being compressible means within said housing with the radially outward end of said compressible means attached to a cutting blade positioned to cut the inner wall of the cylinder opposite the longitudinal groove, said cutting blade being guided by a cover of said housing having a slot whereby to prevent twisting of said blade, said blade being positioned so that upon injection of a solution said weakened groove of said wall is cut along the length thereof as the injection proceeds, there being provided oppositely disposed stop means adjacent the open end of said cylinder, said oppositely disposed stop means being spaced from each other a distance less than the diameter of the piston but at least as great as the diameter of the disc, said disc having a smaller diameter than the maximum diameter of the piston, said piston being made of compressible material.

6. A syringe according to claim 5, in which the oppositely disposed means adjacent the open end of the cylinder comprises a disc affixed to the support flanges having a circular opening with a diameter less than the diameter of the compressible piston but greater than the diameter of the disc adjacent the piston.

7. A syringe according to claim 6, in which the circular opening of the oppositely disposed stop means has a greater diameter at its upper end than at its bottom end, adjacent the open end of the cylinder, so as to have a frusto-conical shape with the diameter of the smallest opening being less than the diameter of the piston.

8. A syringe according to claim 7, in which the support flanges and oppositely disposed stop means are integrally formed.

9. A syringe according to claim 5, in which the piston is made of rubbery-like material, said piston being attached to the adjacent disc by a barb embedded in the disc.

* * * * *